(12) United States Patent
Angelillo

(10) Patent No.: US 11,213,365 B1
(45) Date of Patent: Jan. 4, 2022

(54) ARTHROCENTESIS KIT DEVICE

(71) Applicant: Michael Angelillo, Plantation, FL (US)

(72) Inventor: Michael Angelillo, Plantation, FL (US)

( * ) Notice: Subject to any disclaimer, the term of this patent is extended or adjusted under 35 U.S.C. 154(b) by 568 days.

(21) Appl. No.: 16/251,042

(22) Filed: Jan. 17, 2019

Related U.S. Application Data

(63) Continuation-in-part of application No. 14/072,168, filed on Nov. 5, 2013, now abandoned, which is a continuation-in-part of application No. 13/111,546, filed on May 19, 2011, now abandoned.

(60) Provisional application No. 61/346,121, filed on May 19, 2010.

(51) Int. Cl.
| | |
|---|---|
| *A61B 5/00* | (2006.01) |
| *A61B 50/33* | (2016.01) |
| *A61B 50/30* | (2016.01) |
| *A61B 50/20* | (2016.01) |

(52) U.S. Cl.
CPC .............. *A61B 50/33* (2016.02); *A61B 50/20* (2016.02); *A61B 2050/3008* (2016.02)

(58) Field of Classification Search
CPC .. A61B 50/33; A61B 50/20; A61B 2050/3008
USPC ......................................... 600/573, 575, 583
See application file for complete search history.

(56) References Cited

U.S. PATENT DOCUMENTS

| | | | | | |
|---|---|---|---|---|---|
| 3,013,656 | A | * | 12/1961 | Murphy, Jr. ......... | B65D 81/027 206/572 |
| 3,203,540 | A | * | 8/1965 | Kalt .......................... | B01L 1/52 206/569 |
| D202,599 | S | * | 10/1965 | Goyke ......................... | D24/230 |
| 4,122,947 | A | * | 10/1978 | Falla ...................... | A61G 12/00 206/569 |
| 4,170,300 | A | * | 10/1979 | Pick ........................ | A61B 50/33 206/365 |
| 4,226,328 | A | * | 10/1980 | Beddow ................... | A61F 17/00 206/364 |
| 4,523,679 | A | * | 6/1985 | Paikoff ..................... | A61L 2/04 206/363 |
| 4,576,185 | A | * | 3/1986 | Proud ................... | B01L 3/5082 600/573 |
| 4,595,102 | A | * | 6/1986 | Cianci .................... | A61B 50/33 206/370 |

(Continued)

*Primary Examiner* — May A Abouelela
(74) *Attorney, Agent, or Firm* — David P. Lhota, Esq.; Lhota & Associates, P.A.

(57) ABSTRACT

An arthrocentesis kit and method for using the kit including a procedure tray having all the necessary contents in one tray to reliably perform an arthrocentesis procedure and deliver the fluid samples to a laboratory for analysis, allowing the physician to order delivery of the tray and perform the procedure at the bedside of the patient by using the tray to simultaneously collect and send the synovial fluid collected to a laboratory for all diagnostic testing, thus enhancing the reliability of proper diagnosis thereby allowing crucial orthopedic surgeons, rheumatologists, internists, emergency room physicians and family practitioners to minimize mistakes caused by delays and mistakes attributable to not having all the arthrocentesis kit tools together and readily available for bedside or emergency room treatment. The instant invention also allows a physician to dispose safely excess fluid in the reservoir, which takes advantage of the fact that bodily fluids quickly solidify into waste fluid for controlled disposal.

18 Claims, 7 Drawing Sheets

(56) References Cited

U.S. PATENT DOCUMENTS

| | | | | |
|---|---|---|---|---|
| 4,777,964 A * | 10/1988 | Briggs | A61B 5/150022 | 206/569 |
| 4,886,071 A * | 12/1989 | Mehl | C12Q 1/04 | 600/573 |
| 4,980,129 A * | 12/1990 | Columbus | B01L 3/5082 | 422/430 |
| 5,020,665 A * | 6/1991 | Bruno | A61M 5/3205 | 206/363 |
| 5,022,409 A * | 6/1991 | Goldstein | A61B 10/0051 | 206/569 |
| 5,038,938 A * | 8/1991 | Berndt | A61M 1/0001 | 206/571 |
| 5,117,981 A * | 6/1992 | Crawford | E06B 9/44 | 206/570 |
| 5,190,049 A * | 3/1993 | Briggs | A61B 5/150022 | 600/573 |
| 5,388,699 A * | 2/1995 | Ratajczak | A61B 10/007 | 206/438 |
| 5,456,361 A * | 10/1995 | Walsh | A45C 11/005 | 132/315 |
| 5,507,279 A * | 4/1996 | Fortune | A61M 16/0472 | 128/200.26 |
| 5,529,189 A * | 6/1996 | Feldschuh | A61M 5/31511 | 206/365 |
| 5,718,245 A * | 2/1998 | Horn | A61F 15/001 | 128/897 |
| 5,738,220 A * | 4/1998 | Geszler | A61N 1/056 | 206/365 |
| 5,779,053 A * | 7/1998 | Partika | A61B 50/33 | 206/370 |
| 5,786,227 A * | 7/1998 | Charlton | B01L 3/502 | 210/359 |
| 5,833,057 A * | 11/1998 | Char | B65D 77/0413 | 206/204 |
| D422,141 S * | 4/2000 | Dembicks | D3/201 | |
| 6,112,900 A * | 9/2000 | Adkins, Jr. | A45C 11/005 | 206/232 |
| 6,116,426 A * | 9/2000 | Slonim | A61F 17/00 | 206/499 |
| 6,152,887 A * | 11/2000 | Blume | A61B 10/0045 | 600/573 |
| 6,171,260 B1 * | 1/2001 | Hochmeister | A61B 10/0096 | 206/569 |
| 6,176,836 B1 * | 1/2001 | Trudil | A61B 10/0096 | 206/363 |
| 6,264,619 B1 * | 7/2001 | Ferguson | A61B 5/15003 | 206/569 |
| D450,391 S * | 11/2001 | Hunt | D24/227 | |
| D471,641 S * | 3/2003 | McMichael | D24/227 | |
| 6,629,936 B2 * | 10/2003 | Hung | A61B 5/4288 | 600/573 |
| 6,740,068 B1 * | 5/2004 | Aruffo | A61F 17/00 | 206/570 |
| 6,779,665 B2 * | 8/2004 | Bolanos | A61B 10/0096 | 206/569 |
| 6,840,379 B2 * | 1/2005 | Franks-Farah | A61B 50/31 | 206/232 |
| 6,907,992 B2 * | 6/2005 | McMichael | A61B 50/30 | 206/370 |
| 7,611,670 B2 * | 11/2009 | Wandell | G01N 33/54393 | 422/404 |
| 7,815,123 B2 * | 10/2010 | Conner | G09F 3/0289 | 235/487 |
| 8,048,321 B2 * | 11/2011 | Leach | G01N 33/491 | 210/782 |
| 8,197,420 B2 * | 6/2012 | Patton | A61B 10/0051 | 600/579 |
| 8,342,332 B2 * | 1/2013 | Alhajri | G09B 23/00 | 206/579 |
| 8,802,370 B2 * | 8/2014 | Knapp | B01L 1/52 | 435/6.11 |
| 2001/0007926 A1 * | 7/2001 | Trudil | A61B 10/0096 | 600/573 |
| 2002/0143272 A1 * | 10/2002 | Crawford | A61B 5/157 | 600/573 |
| 2003/0091687 A1 * | 5/2003 | Copelan | A23L 33/30 | 426/2 |
| 2004/0054300 A1 * | 3/2004 | Hung | A61B 10/0041 | 600/573 |
| 2005/0113718 A1 * | 5/2005 | Butler | B01L 9/06 | 600/573 |
| 2005/0130310 A1 * | 6/2005 | Wandell | G01N 33/96 | 436/71 |
| 2005/0281713 A1 * | 12/2005 | Hampsch | A61B 5/150236 | 422/400 |
| 2006/0020227 A1 * | 1/2006 | Moore | A61B 5/150755 | 600/573 |
| 2006/0074347 A1 * | 4/2006 | Eguchi | B01L 1/52 | 600/573 |
| 2006/0167380 A1 * | 7/2006 | Morton | A61B 10/007 | 600/573 |
| 2007/0185410 A1 * | 8/2007 | Fernandes | B01L 3/502 | 600/562 |
| 2007/0208274 A1 * | 9/2007 | Ostrowski | B01L 3/5029 | 600/573 |
| 2007/0208275 A1 * | 9/2007 | Vinogradov | A61B 5/150412 | 600/573 |
| 2007/0208321 A1 * | 9/2007 | Leach | B01L 3/50215 | 604/500 |
| 2007/0289894 A1 * | 12/2007 | Tennant | A61B 10/0096 | 206/569 |
| 2008/0061118 A1 * | 3/2008 | Erdie | B65D 43/0212 | 229/4.5 |
| 2008/0086103 A1 * | 4/2008 | McKiernan | G01K 11/165 | 604/385.02 |
| 2008/0145933 A1 * | 6/2008 | Patton | A61B 5/155 | 435/379 |
| 2008/0171951 A1 * | 7/2008 | Fell | A61M 1/3698 | 600/573 |
| 2008/0208158 A1 * | 8/2008 | Goodman | B65D 81/3862 | 604/408 |
| 2008/0292685 A1 * | 11/2008 | Wang | A61P 9/00 | 424/449 |
| 2008/0293795 A1 * | 11/2008 | Donawho | A61K 31/4184 | 514/394 |
| 2008/0314912 A1 * | 12/2008 | Horsburgh | B65D 59/04 | 220/605 |
| 2009/0054809 A1 * | 2/2009 | Morishita | G01N 1/38 | 600/573 |
| 2009/0281454 A1 * | 11/2009 | Baker | A61M 3/022 | 600/573 |
| 2009/0291449 A1 * | 11/2009 | Knapp, Jr | B01L 3/545 | 435/6.11 |
| 2010/0010372 A1 * | 1/2010 | Brown | A61B 5/150389 | 600/573 |
| 2010/0010373 A1 * | 1/2010 | Wandell | G01N 33/92 | 600/573 |
| 2010/0172797 A1 * | 7/2010 | Gould | A61B 10/007 | 422/400 |
| 2010/0331741 A9 * | 12/2010 | Cioanta | A61N 7/00 | 601/2 |
| 2011/0105872 A1 * | 5/2011 | Chickering, III | A61B 5/150297 | 600/365 |

* cited by examiner

50 — FLUIDS TEST REQUISITION

Account #7203
Synovial Fluid
Bill to: ☐ Physician
☐ Insurance

Patient Information

| Last Name | First Name | MI | DOB | Sex ☐M☐F | Social Security No. |

| Address | City | State | Zip Code | Phone No. |

| Insurance Company Name | Insurance Number | Group Number | Please enclose a copy of the front & back of insurance card |

Physician Information

| Physician Name | | Provider Number: NPI # |

| Address | City | State | Zip Code |

| Phone No. | Fax No. | Physician Signature |

Fluid Site: _____ Date Collected: _____ Time Collected: _____ ICD-9 Code(s): _____
Patient on antibiotics: _____ Yes _____ No (Please check if ordering culture)

☐ COMPREHENSIVE PANEL  [1 LAV + 1 GRN + RED]
Panel Includes: Infection Panel (DETAIL BELOW)
Inflammatory Panel (DETIAL BELOW)

☐ INFECTION PANEL [1 LAV + 1 GRN + RED]  ☐ INFLAMATORY PANEL [1 LAV + 1 GRN + RED]
PANEL INCLUDES:                            PANEL INCLUDES:

| Test Code | Test | CTP Code | Test Code | Test | CTP Code |
|---|---|---|---|---|---|
| 5012 | Gram Stain | 87205 | 6098 | Gram Stain | 83872 |
| 5001 | Culture w/ Sensitivity (Sensitivity only performed if.. | 87071/87187 | 1714 | Gram Stain | 84560 |
| 0633 | Cell Count w/ Differential | 89051 | 8662 | Gram Stain | 809060 |
| 1713 | Glucose | 82945 | 1444 | Gram Stain | 86431 |
| 1418 | Total Protein | 84157 | 1419 1420 | Gram Stain | 86160 x 2 |
| 1417 | LDH | 83615 | 1713 | Gram Stain | 82945 |
| 8941 | Lyme Disease Antibody (IgG, .. | 86618 x 2 | 1418 | Total Protein | 84157 |

| INDIVIDUAL TESTS [1 LAV] | | | INDIVIDUAL TESTS [1 GRN] | | | INDIVIDUAL TESTS [1 RED] | | |
|---|---|---|---|---|---|---|---|---|
| Test Code ☒ | Test | CPT Code | Test Code ☒ | Test | CPT Code | Test Code ☒ | Test | CPT Code |
| 0633 ☐ | Cell Count w/ Differ.. | 89051 | 1713 ☐ | Glucose | 82943 | 5012 ☐ | Gram Stain | 87205 |
| 6098 ☐ | Mucin Clot | 83872 | 1418 ☐ | Total Protein | 84157 | 5001 ☐ | Culture w/ Sensitivity (Sensitivity only perf.. culture is positive) | 87071 87187 |
| 8662 ☐ | Crystal Identification | 89060 | 1417 ☐ | LDH | 83615 | | | |
| | | | 1714 ☐ | Uric Acid | 84560 | | | |
| Comments: | | | 1444 ☐ | Rheumatoid Factor.. | 86431 | 8941 ☐ | Lyme Disease Antibody (IgG, IgM) | 86618 |
| | | | 1419 ☐ | Compent, C3, C4 | 86160 | | | |

VERIFY PATIENT INSURANCE COVERAGE

*MAILING INSTRUCTION TO SEND SAMPLES*

1. Fill out requisition slip with all required information. Include insurance information and test orders with appropriate diagnosis.

2. Label all tubes with TWO patient identifiers: Patient's FULL name with a second identifier being for example the date of birth, social security number, medical record number etc. and information used should also be on the enclosed requisition.

3. Place the labeled tubes in the red biohazard bag.

4. Wrap enclosed absorbent pad around the tubes before placing them in the biohazard bag.

5. Fold completed requisition, wrap around the bag and place in the mailing canister.

6. Place canister in FedEx bag.

7. Separate mailing label placing shipping portion on the outside of the FedEx bag and keeping sender copy for your records.

8. Call for pick up or drop at any FedEx location.

FIG. 5

ARTHROCENTESIS KIT DEVICE

CROSS REFERENCE TO RELATED APPLICATIONS

This application is a continuation-in-part of application Ser. No. 14/072,168 filed Nov. 5, 2013 which is a continuation-in-part of application Ser. No. 13/111,546 filed May 19, 2011 which claims the benefit of provisional patent application Ser. No. 61/346,121 filed May 19, 2010.

STATEMENT REGARDING FEDERALLY SPONSORED RESEARCH OR DEVELOPMENT

N/A

COPYRIGHT NOTICE

A portion of the disclosure of this patent document contains material that is subject to copyright protection. The copyright owner has no objection to the facsimile reproduction by anyone of the patent document or patent disclosure as it appears in the Patent and Trademark Office patent file or records, but otherwise reserves all copyrights rights whatsoever.

BACKGROUND OF THE INVENTION

1. Field of the Invention

This invention relates generally to an arthrocentesis kit, and more particularly, to an arthrocentesis kit having all the instruments required to collect synovial fluid from a joint capsule for joint aspiration in a one readily available tray having all the tools necessary to enhance the ability for and reduce the liability when diagnosing gout, arthritis, synovial-based infections and numerous other rheumatological collagen vascular conditions.

2. Description of the Background Art

According to the Medicare Statistical Data Base, which is comprised of Medicare based patients, there are well over 5 million documented arthrocentesis procedures currently being done on an annual basis. When combined with other statistical data from other types of insurance companies it is estimated that over 20 million procedures are done in doctor's offices, hospitals and emergency rooms each year. What is alarming is that it is also estimated that over 75% of these procedures are not done properly, resulting in an increase in the number of malpractice occurrences throughout the country. This adverse result is in part because the synovial fluid being analyzed is not being properly done or submitted as a result of the improper placement of the synovial fluid when it is sent to a lab for analysis. This occurs because of wrong tube placement or improper delineation of the tubes being used. This problem is also believed to originate from the wrong diagnostic supplies not being readily available at the time of the procedure which contributes to improper diagnosis. As a result of these inadequacies, the arthrocentesis procedures are routinely being done improperly, which has led to a delay in diagnosis, wrong diagnosis, wrong therapies and, or wrong treatments. This is not only problematic for medical personnel performing the procedure, but the labs responsible for processing synovial fluid.

Pursuant to the background art, medical kit related patents have been allowed. For instance, U.S. Pat. No. 6,691,886, issued to Berndt, et al., discloses a resealable plastic packaging container with hook and loop closure. U.S. Pat. No. 5,709,305, issued to Essig et al., discloses a dispenser for solid pharmaceutical preparations. Based on the foregoing, the noted prior art fails to disclose the instant invention.

If there existed a comprehensive kit comprising a tray with all the tools and instructions readily available to properly perform arthrocentesis procedures and submit the synovial fluid to a laboratory for proper evaluation, it would enable medical personnel to perform the procedure with the proper tools readily available, to make an accurate and timely diagnosis and reduce the number of inaccurate results or the return of fluids that cannot be analyzed because of reliability concerns. However, such a comprehensive arthrocentesis kit that adequately and effectively resolves these issues is not known.

Accordingly, there exists a need for such a readily available arthrocentesis kit that has all the tools needed for synovial fluid extraction and submissions to labs in one readily available kit. If such a kit existed it would reduce medical errors and expedite the proper diagnosis and hence proper treatment. Moreover, such a kit would reduce liability for the physicians. It is believed that the contemplated arthrocentesis kit of the instant invention could become the standard in synovial analysis and treatment, which would also result in saving lives. If such a kit were available, it would allow physicians to order or request a tray at the bedside of a patient, would be readily available with all the necessary tools for use by physician offices, emergency rooms, hospitals or clinics and would result in significant cost savings to the hospital and patient. The instant invention would provide all the components required to perform proper arthrocentesis procedures for reliable diagnostics as well provide a unique reservoir for the easy disposal of waste fluids. Unfortunately, there are no arthrocentesis kits known that contemplate or accomplish these objectives. Therefore, there exists a need for an arthrocentesis kit that resolves these issues. It is, therefore, to the effective resolution of the aforementioned problems and shortcomings of the prior art that the present invention is directed. The instant invention addresses this unfulfilled need in the prior art by providing an arthrocentesis kit as contemplated by the instant invention disclosed herein.

BRIEF SUMMARY OF THE INVENTION

In light of the foregoing, it is an object of the present invention to provide an arthrocentesis kit that provides a procedure tray system having all the necessary contents in one tray for reliably performing an arthrocentesis procedure.

It is also an object of the instant invention to provide a kit and method for reliably performing and reporting arthrocentesis procedures.

It is another object of the instant invention to provide a kit and method for reliably performing arthrocentesis procedures and submitting results to a medical test laboratory.

It is an additional object of the instant invention to provide a kit and method for receiving reliable test laboratory results from the laboratory.

In light of these and other objects, the instant invention comprises an arthrocentesis kit and method for using the kit including a procedure tray having all the necessary contents in one tray to reliably perform an arthrocentesis procedure and deliver the fluid samples to a laboratory for analysis. This allows the physician to order delivery of the tray and perform the procedure at the bedside of the patient. By using the tray the physician can simultaneously collect and send the synovial fluid collected to a laboratory for all diagnostic testing, thus enhancing the reliability of proper diagnosis. The instant invention allows crucial orthopedic surgeons, rheumatologists, internists, emergency room physicians and family practitioners to minimize mistakes caused by delays and mistakes attributable to not having all the arthrocentesis kit tools together and readily available for bedside or emergency room treatment. The instant invention also allows a physician to dispose safely excess fluid in the reservoir, which takes advantage of the fact that bodily fluids quickly solidify into waste fluid for controlled disposal.

In accordance with these and other objects, which will become apparent hereinafter, the instant invention will now be described with particular reference to the accompanying drawings.

BRIEF DESCRIPTION OF THE SEVERAL VIEWS OF THE DRAWINGS

FIG. 4 shows a recordation document used in accordance with the preferred embodiment of the instant invention.

FIG. 5 shows an instruction document used in accordance with the preferred embodiment of the instant invention.

DETAILED DESCRIPTION OF THE INVENTION

Figure 1:
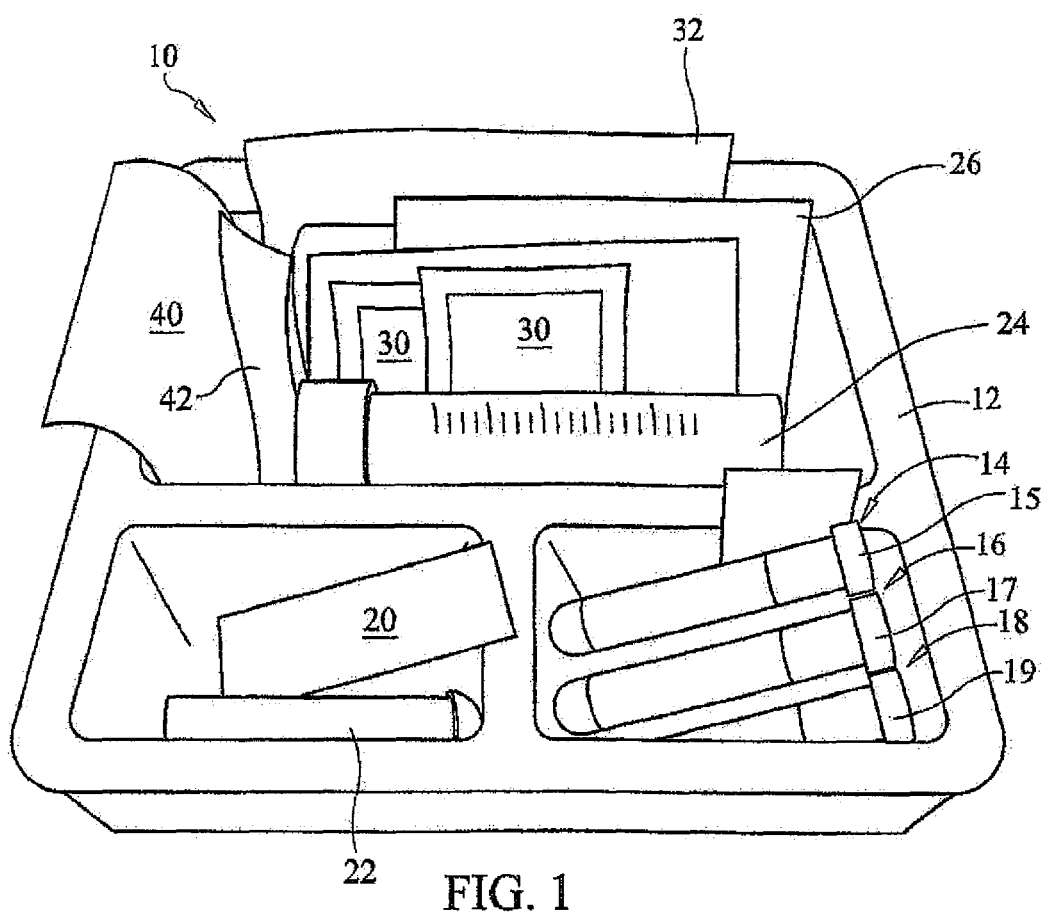
FIG. 1 is a perspective view of the arthrocentesis kit in accordance with the preferred embodiment of the instant invention.

With reference to the drawings, FIGS. 1 to 8 depict the preferred embodiment of the instant invention which is generally referenced as an arthrocentesis kit and, or by numeric character 10. The arthrocentesis kit 10 provides a procedure tray having all the necessary contents in one tray to reliably perform an arthrocentesis procedure and deliver the fluid samples to a laboratory for analysis. This allows the physician to order delivery of the tray and perform the procedure at the bedside of the patient. By using the tray 12 the physician can now simultaneously collect and send the synovial fluid collected to a laboratory for all diagnostic testing, thus enhancing the reliability of proper diagnosis. The instant invention 10 allows crucial orthopedic surgeons, rheumatologists, internists, emergency room physicians and family practitioners to minimize mistakes caused by delays and mistakes attributable to not having all the arthrocentesis kit tools together and readily available for bedside or emergency room treatment. The instant invention 10 also allows a physician to dispose safely excess fluid in the reservoir, which takes advantage of the fact that bodily fluids quickly solidify into waste fluid for controlled disposal.

With reference to FIGS. 1-8, the arthrocentesis kit 10 of the instant invention comprises a tray 12 having a plurality of receptacles, a liquid absorption pouch 25, a plurality of collection tubes 14, 16 and 18, a first needle 20, a second needle 22, at least one syringe 24, a sterile gauze pad 26, alcohol pads 30, providine-iodine swabsticks 32, an absorption sponge 40, a sterile bandage device 42, mailing tube/canister 46 for the collection tubes 14-18, a specimen bag 70, an express mail bag 48, a fluid test requisition form 50 and instructions for use. The instant invention may also comprise an absorption pouch 25 or 44 and, or a mailing instructions form 60 for sending samples to a laboratory for analysis. The tray 12 comprises a partitioned storage container for securely placing all the arthrocentesis tools 14-70 needed for drawing and transporting synovial fluid. The collection tubes 14, 16, 18 comprise three 3 ml tubes with different colored tops 15, 17, 19 that differentiate the contents. For instance, one collection tube 14 may comprise a purple/violet top 15 indicative of $K_2$ EDTA. The EDTA fluid in this tube 14 prevents clotting and is sent for microscopy, mucin clot analysis and cell count with differentials and crystals. Another collection tube 16 may comprise a red top 17 indicative of blood serum. The red tube 16 has no additives and is sent to a lab for chemistry, microbiology, protein, glucose, Lyme, Chlamydia etc. Still another collection tube 18 may comprise a green top 19 that could be indicative of Lithium or Sodium Heparin. Sodium Heparin prevents clotting and does not crystallize. This fluid is sent to a laboratory for analysis of glucose, crystals, T-protein, LDH, uric acid, RA and $C_3/C_4$. The size of the collection tubes 14-18 may vary in volume.

With reference to FIGS. 1-8, the tray 12 of the instant invention preferably includes and holds at least the following:

1 Package of 3 Providone-Iodine Swabsticks 32;
2 Alcohol preparation pads 30;
1 Sterile Gauze 26;
1 Sterile bandage 42;
1 Syringe for synovial fluid aspiration in a 20-50 cc luer-lock syringe 24;
1 5 cc Syringe 21 to inject and numb the skin;
1 18-gauge needle, 1½ inches long 20;
1 22 gauge needle, 1½ inches long for anesthetics 22;
1 Red top 3 ml collection tube; 14/15
1 Lavender top 3 ml collection tube 16/17;
1 Green top 3 ml collection tube 18/19;
1 sponge 40;
1 liquid absorber used in shipping 13;
1 mailing tube/canister used for shipping 46;
1 Express Mail mailer bag 48;
1 Biohazard Specimen bag 70 used for shipping and holding the canister 46;
1 Requisition slip included with shipping 50; and
1 Mailing label for mailing test results or samples.

Figure 2:
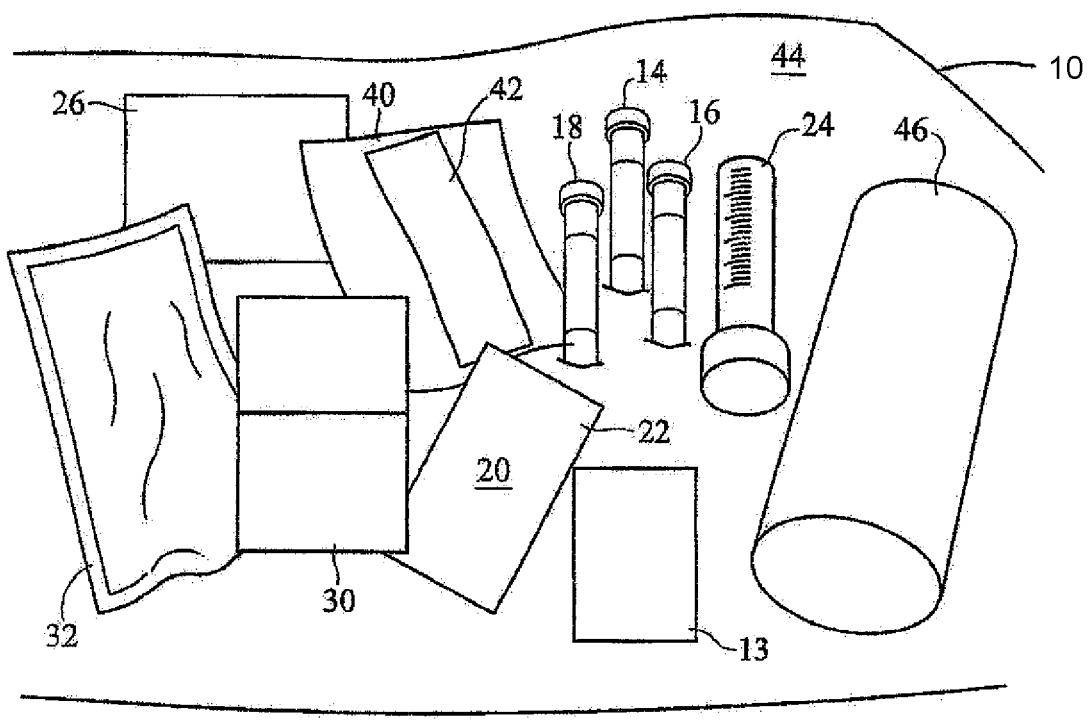
FIG. 2 is a perspective exploded view of the arthrocentesis kit in accordance with the preferred embodiment of the instant invention.
Figure 3:
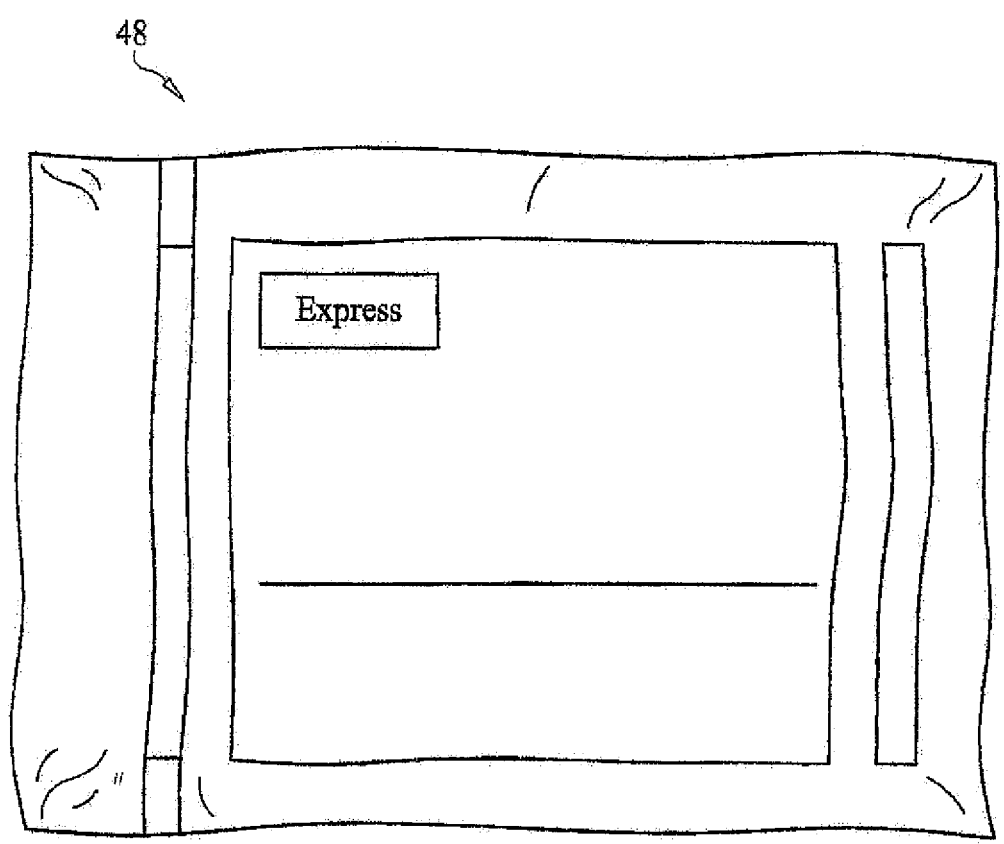
FIG. 3 is a perspective exploded view of mailing insert for sending kit fluids and information to a testing laboratory in accordance with the preferred embodiment of the instant invention.
Figure 6:
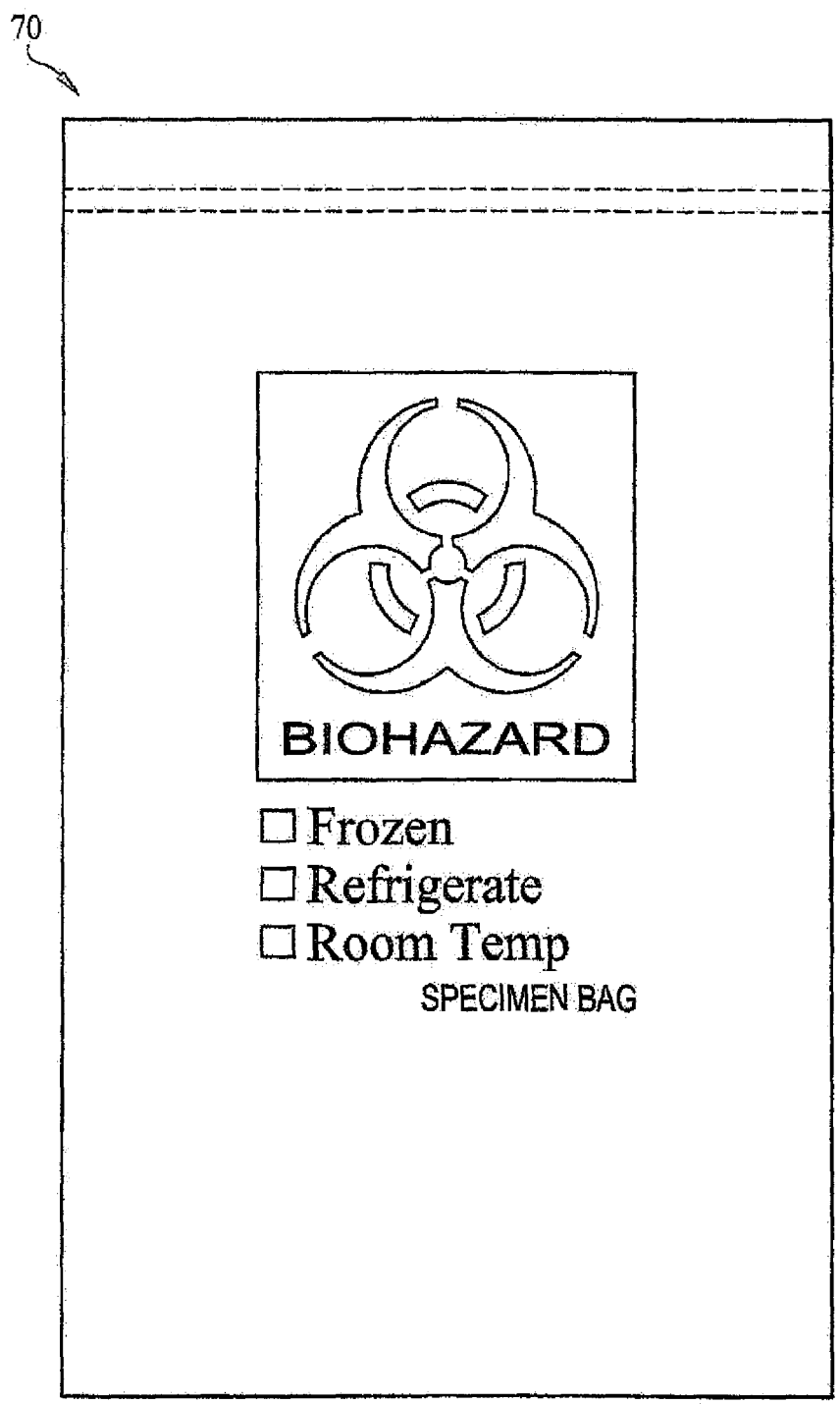
FIG. 6 shows a specimen bag for sending fluid samples to a laboratory in accordance with the preferred embodiment of the instant invention.

Still referring to FIGS. 1 and 2, the other components are as follows. The first needle 20 comprises a 22 gauge 1.5 inch needle and the second needle 22 comprises an 18 gauge 1.5 inch needle. The syringe 24 preferably comprises a 20-50 cc luer-lock syringe 24. The needles 20, 22 may be used with the syringe 24 for aspirating synovial fluid or injecting anesthetics. The first needle 20 is preferably used for anesthetics. The sterile gauze pad 26 preferably comprises a 3 inch×3 inch gauze pad as is known in the art. The alcohol pads 30 comprise a 1.25 inch×1.5 inch sterile alcohol prepared pad with 70% isopropyl alcohol and that is latex free. The providone-iodine swabsticks 32 comprise three 4-inch saturated swabsticks packaged in a sterile bag. The kit 10 also comprises an absorption sponge 40 and an absorbent pouch 44 to absorb and retain bodily fluid drippings. The absorption sponge 40 is used to collect synovial fluid remaining in the syringe 24 after synovial fluid is placed in the collection tubes 14, 16 and 18 and preferably expands up to approximately ten times its unsaturated size. The mailing tube/canister 46 of the arthrocentesis kit 10 comprises a 2 inch diameter and 5 inch long tube 46 for placing the collection tubes 14-18 for mailing to the lab. The kit 10 may also include a specimen bag 70, as shown in FIG. 6, for placing the mailing tube 46 with the collection tubes 14-18.

Figure 7:
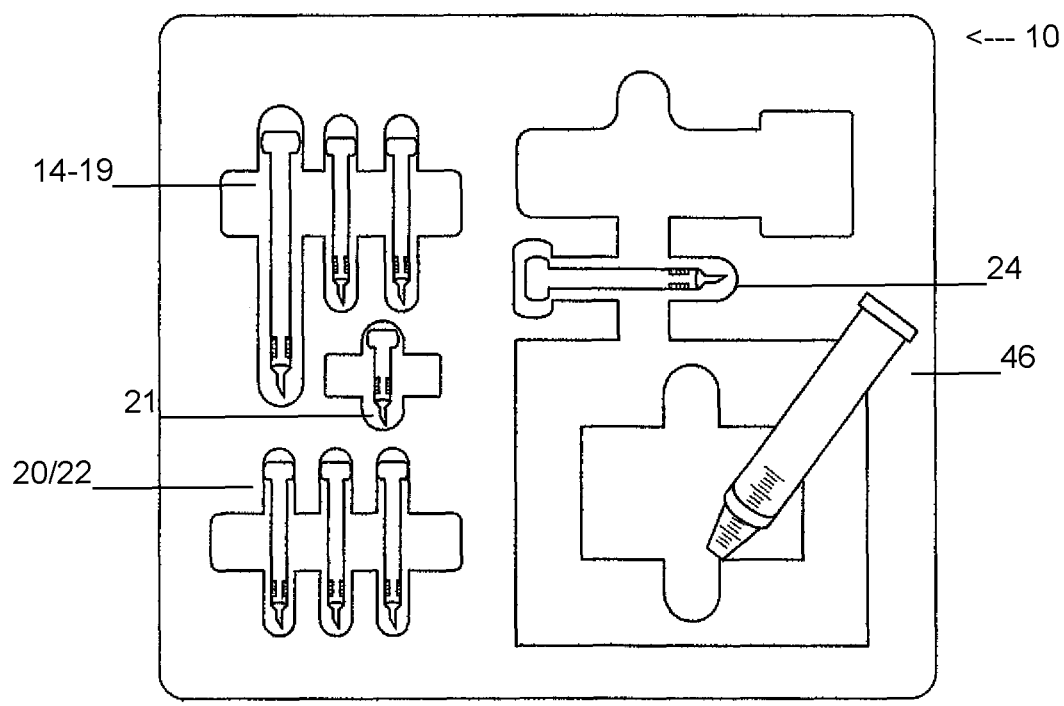
FIG. 7 is a perspective view of the arthrocentesis kit in accordance with the alternative embodiment of the instant invention.
Figure 8:
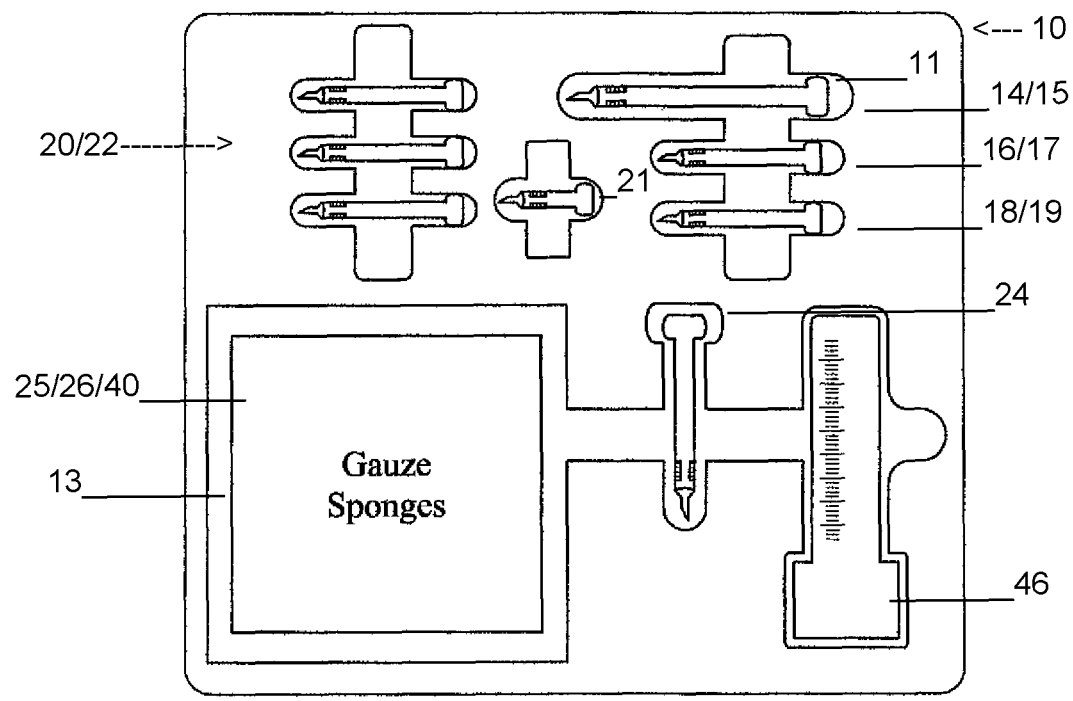
FIG. 8 is another perspective view of the arthrocentesis kit in accordance with the alternative embodiment of the instant invention.

With reference to FIGS. 7 and 8, in an alternative embodiment the tray 12 may comprise contoured receptacles 80 that are shaped to accommodate and coincide with the shape of the syringes 24, collection tubes 14-18, absorption sponge 40, needles and an anesthetic capsule 90. The contoured receptacles 80 comprise a first syringe contoured receptacle 82 shaped like a first syringe 24, a second contoured syringe receptacle 84 shaped like a second smaller syringe 24, a first collection tubes receptacle 83 shaped like a first set of three collection tubes, a second collection tubes receptacle 85 shaped like a second set of three collection tubes, an absorption sponge receptacle 86 having a rectangular shape and synovial fluid reservoir 88 and an anesthetic receptacle 87 shaped, at least in part, like an anesthetic capsule container 90. With reference to FIG. 8, the absorption sponge receptacle is shaped like and to hold an absorption or gauze sponges 40 and to accommodate the expansion of the absorption sponge 40.

With reference to FIGS. 4 and 5, the kit 10 further comprises a "Fluids Test Requisition" form 50 and patient insurance coverage form 60. The requisition form 50 provides patient information, physician information and identification codes and information for identifying the contents of the kit 10 sent to a laboratory for testing. The patient insurance coverage form 60 provides instructions for submitting the laboratory costs to an insurance company.

With reference to FIGS. 1-8, the arthrocentesis procedure, aspiration or injection may be performed when there is fluid or an effusion or inflammation which is present in a joint or bursa. Inflammation is characterized by the presence of warmth, pain and or swelling. The indications to perform an arthrocentesis includes but not limited to:
  To drain a traumatic hematoma.
  To remove fluid for diagnostic purposes.
  To drain accumulated fluid and relieving pain by decompression of the area.
  To decompress a joint when pyarthroses is present and instill antibiotics.

The arthrocentesis procedure of the instant invention 10 is also known as joint aspiration by the puncture of a joint space on the body with a needle in order to aspirate (withdraw) accumulated fluid from the joint. This procedure is completed using a sterile technique, which may be explained step-by-step on an instruction sheet provided with the kit 10. After the fluid is aspirated it is placed in the proper collection tube 14, 16 or 18 to be sent to a laboratory for analysis. Once the fluid is analyzed a prompt diagnosis can be performed with a diagnostic chart available in the tray 12. The suggested instructions for the arthrocentesis procedure are as follows:
  1) Clean skin overlying affected joint with Providine-iodine swabstick (32).
  2) Anesthetize affected targeted area with lidocaine using 22 gauge needle and 3 cc syringe (20).
  3) Puncture skin into joint using 18 gauge needle (22) and 50 cc syringe (24).
  4) Aspirate contents of joint into 50 cc syringe (24) and remove from joint.
  5) Puncture each collecting tube (14, 16 or 18) with synovial fluid contents for analysis and culture if necessary for diagnostic studies ordered.
  6) Discard excess fluid in reservoir provided on absorbant pad (40) if required.

With reference to FIG. 5, the arthrocentesis kit 10 of the instant invention also comprises a mailing instructions form 60 for sending samples to a laboratory for analysis and a reminder to verify patient insurance coverage to facilitate payment by insurance companies. The instructions form 60 first instructs verification of patient insurance coverage. Still referring to FIG. 6, the instructions 60 first require that the fluid test requisition form 50 be completed with all the requested information in the appropriate fields including insurance information and test orders with the appropriate diagnosis. Second, all tubes are labeled with two patient identifiers, as instructed in FIG. 5. Under steps 3 and 4, the liquid absorption pouch 13 found in the kit 10 and the labeled tubes 14, 16 and 18 are placed in the red biohazard specimen bag 70. In the event a tube 14, 16 or 18 breaks, the absorption pouch 13 will collect the lost liquid. Under step 5, the completed requisition form 50 is folded, wrapped around the specimen bag 70 and placed in the mailing tube 46. The tube 46 is then sent to a laboratory for analysis. If the laboratory is on-site, such as in a hospital, it is delivered through an inter-office mailing system. If the samples are drawn at a facility without a laboratory, such as at a doctor's office, and are to be analyzed by an off-site laboratory, then steps 6-8 of the instruction form 60 apply. Under steps 6-8, the tube 46 is placed in the FedEx® bag 48 provided in the kit 10, the shipping label is placed on the bag 48 and FedEx® is called for pick-up.

When a physician bills a patient they will bill an Insurance Company, or Medicare. Today Medicare is the standard on what to bill a procedure for because they have instituted CPT Codes. CPT Codes stand for Correct Procedural Terminology. CPT Codes are five digit numbers created by the American Medical Association for medical billing purposes. All medical services and procedures have a unique Code which provide greater ease and uniformity for health care providers and insurance companies.

With reference to FIGS. 1-8 and the forgoing descriptions, the instant invention 10 is a kit 10 with devices 12-70 for reliably and effectively aspirating, categorizing, instruction and tracking devices bodily fluids which is more specifically related to the entire method of aspirating synovial fluid from the various joints of the body and then having the capability to make a medical diagnosis for disease, inflammation or infection of the joint that is being aspirated. This is possible because of all the contents 12-70 provided in the arthrocentesis kit 10. The kit 10 uniquely provides instruction of how to mail and send the synovial fluid using the contents 12-70 of the kit 10 provided, once the synovial fluid is aspirated and instruction using the requisition form 50 of how to make a specific diagnosis or disease from that synovial fluid aspirated, by coordinating the specific color vials/tubes 14-19 that the synovial fluid has to be placed in including contents to mail the synovial fluid properly. The inventive kit 10 enables and provides the user with all of the kit contents 12-70 for a medical professional who is doing the aspiration to not only perform the aspiration properly but then enables the transport of synovial fluid in vials 14, 16, 18 contained in the kit 10 using FedEx bags 48 for diagnostic testing using specific colored test tubes 14-19 provided for this diagnostic testing to a laboratory for those specific tests ordered. The kit 10 also enables the capability to discard excess synovial fluid specifically so spillage does not take place, using an absorbable sponge 40 provided in the kit 10 to prevent the spread of infectious wastes. This enables one to dispose of the excess fluid into a red bag mandated by hospital protocols to prevent spread of potential infectious wastes by preventing leakage. Putting excess synovial fluid in a red waste bag could spill out if it is not absorbed properly when discarded. Also provided is an original copyrighted requisition sheet or form 50 specifically designed to coordinate and assist the medical professional aspirating the joint in question to coordinate which synovial test should be ordered by instructing the medical professional to place the synovial fluid in a specific color top test tube 14-19 specific for that particular test ordered to prevent errors, so that specific diagnostic test is processed properly using the specific color top vial tube. All diagnostic lab tests cannot be processed in all of the same color test tubes because each diagnostic test requires different test tubes making this kit unique. Once the tubes 14, 16, 18 contain synovial fluid that was aspirated then the tubes 14-19 can be mailed using FedEx properly using the instruction sheet 60 provided. Specifically, the tubes with colored tops 14-19 are placed in a biohazard specimen bag 70 with the liquid absorber 25/26/44 used for shipping to prevent spillage while shipping in the canister/mailing tube 40 provided in the kit 10 with the requisition form 50 to the lab for analysis.

Still referring to FIGS. 1-8, the instant invention 10 comprises an arthrocentesis kit 10 for performing an arthrocentesis procedure which enables medical professionals to withdraw synovial fluid from a joint which than can be delivered or mailed to the laboratory for analysis for various diagnostic test analysis. The kit 10 comprises a tray 12 having several tray receptacles: one receptacle to hold the three collection test tubes 14, 16 18 which have red 15, lavender 17 and green 19 tops. The lavender colored tube 16/17 has a chelating agent inside, such as an EDTA chelating agent. When combined synovial fluid is placed directly in this tube 16 you can test the synovial fluid for microscopy, mucin clot analysis and cell count with differential and crystal analysis/identification. The green top vial 18/19, which has lithium heparin in it, is used for testing for glucose, total protein, Lactate Dehydrogenase, uric acid, rheumatoid factor, and complement C3 and C4. The red top vial 14/15 has no additive in it and is used for testing for gram stain, culture w/sensitivity, and Lyme disease only. The kit 10 contains one 50 cc syringe 24 for aspirating the synovial fluid from the joint. One iodine-based swab stick 32 is used to clean off the skin site to be aspirated to prevent infection. One absorption sponge 40 for absorbing the excess synovial fluid aspirated from joint which is placed in the receptacle to prevent spillage of infectious wastes which doubles in size inside the receptacle tray. One mailing canister 46 for transporting said collection tubes 14-19 to the laboratory. One receptacle tray 12 to hold a 5 cc syringe 21 used to inject and numb the skin. One receptacle for holding the absorption sponge. A fluid requisition form comprising of what colored coated vials or tubes corresponding to be used for what synovial tests ordered. This insures that no errors will be sent to the lab. This means that certain tests have to be sent in certain test tubes so those said tests could be analyzed properly. The kit includes a sterile bandage 42. This is used to be placed over the puncture site on the skin after the synovial fluid was withdrawn to prevent infection until the puncture site closes or heals. A specimen bag 70 is included in the kit 10 so the test tubes 14-19 filled with synovial fluid can be placed in this bag 70 for shipping to the lab. Then diagnostic testing could be processed successfully. An instruction sheet 60 is provided in the kit 10 which gives instruction of how to transport or mail the test tubes 14-19 that are being shipped to the lab properly after they are filled with synovial fluid.

Still referring to FIGS. 1-8, two needles are also in kit. One needle 20 is an 18 gauge, 1½ inch needle which is connected to the 50-cc syringe 24 to aspirate the synovial fluid from the joint in question. This is a bigger bore needle so the viscous synovial fluid material could be aspirated into the syringe from the joint. The thinner 22 gauge needle 22, 1½ inch needle is connected to the 5 cc syringe 21 to anesthize the area on the skin directly over the joint that is going to be aspirated. Enclosed in the kit 10 is an express FedEx mailing bag 48 for mailing the synovial fluid filled test tubes 14-19 to the laboratory. This bag is used so the collection vials/tubes could get to the lab in a timely manner. The kit 10 contains a liquid absorption pouch 25 which is placed in the canister 46 to be mailed with the test tubes 14-19. This will absorb any synovial liquid so no leakage occurs if the test tubes break while mailing the canister 46. One alcohol prep pad 30 is included in the kit which is used to clean the skin to prevent bacterial from entering into the joint before piercing the skin to enter the joint being aspirated. One receptacle in the kit 10 holds the 50 cc syringe 24 in place. This receptacle was molded to hold the 50 cc syringe 24 in place for easy withdrawal from the kit 10 to use. One receptacle in the kit 10 to hold the 5 cc syringe 21 in place. This receptacle was molded to hold specifically the 5 cc syringe 21 in place for easy withdrawal from the kit to use. The kit 10 provides three receptacles in the shape of the three different colored test tubes with or without caps 14-19. These receptacles are contoured in the same shape of the test tubes 14-19 to hold the test tubes in place in the kit 10. This makes it easy to take the test tubes 14-19 out of the kit 10. The kit 10 has a receptacle to hold the mailing canister 46 in place in the kit 10. In the kit 10 is a receptacle to hold the absorptive sponge 40. This receptacle allows a place to put the extra synovial fluid with the absorptive sponge so the sponge can expand when absorbing the excess synovial fluid so no spillage occurs and no wastes are leaked. The kit 10 has a specific synovial fluid reservoir 13. This reservoir 13 holds excess synovial fluid with the absorptive sponge inside it to prevent spillage.

Referring to FIGS. 1-8, the method for performing, delivering and receiving arthrocentesis tests and results comprising the steps of this kit 10 having a tray 12 with multiple receptacles, an absorptive sponge 40 in the kit for absorbing excess synovial liquid, the kit 10 also is comprised of one 22 gauge 1½" needle 22 which attaches to a 5 ml syringe 21 to anesthetize the skin above the joint being aspirated. A 50 cc syringe 24 to aspirate the synovial fluid. An 18 gauge 1½" needle 20 to be connected to the 50 cc syringe to aspirate the synovial fluid. One swab stick 32 to clean the skin over the joint being aspirated to reduce the potential risk of infection. One absorptive pouch 25 to absorb excess synovial fluid sent to the lab in mailing in the canister to prevent spillage. The kit 10 has a canister tube 46 to place the tubes 14-19 being sent to the lab for mailing. The express mailing bag 48 for mailing the tubes 14-19 to the laboratory for analysis. A fluid requisition form 50 to identify what tests to be placed in certain said tubes for analysis. All of the tubes 14, 16, 18: lavender top 17, red top 15 and green top 49 tubes including the requisition form, absorptive sponge 40 that is put in the canister 46 for mailing and then put in the express mailing bag 48 for mailing to the lab for diagnostics. The method of the instant invention 10 includes mailing an instructions sheet 60 to the professional who is doing the procedure so the synovial fluid filled test tubes 14-19 can be sent to the lab of choice for analysis properly; placing a liquid absorption pouch 25 or 44 in the canister tube 46 for absorbing any potential liquid preventing any potential spill from any of the collection tubes that are being sent to the lab in case of breakage; providing at least one alcohol pad 30 for cleaning the area of the skin of the patient to be pierced by the 5 ml needle 21 over the joint to be aspirated; and, or providing a fluid requisition form 50 which is comprised of color corresponding color tube caps 15, 17, 19 to prevent mistakes. This allow a provider doing the aspiration to know what test goes into what tubes 14, 16, 18 for analysis to the lab.

The instant invention has been shown and described herein in what is considered to be the most practical and preferred embodiment. It is recognized, however, that departures may be made therefrom within the scope of the invention and that obvious structural and/or functional modifications will occur to a person skilled in the art.

What is claimed is:

1. An arthrocentesis kit for performing an arthrocentesis procedure that aspirates synovial fluid from a person's joint, delivering collected synovial fluid to a laboratory for analysis and receiving laboratory results, said kit comprising:
    a tray, said tray having a plurality of tray receptacles;
    said tray receptacles including an excess fluid tray receptacle for placing excess synovial fluid aspirated from a person;
    a gauze pad, storable in said excess tray;
    a plurality of collection tubes for holding the synovial fluid aspirated from the person's joint, said tubes including a first collection tube having a first removable cap having a first color, a second collection tube having a second removable cap having a second color and a third collection tube having a third removable cap having a third color; said first color, said second color and said third color comprising different colors wherein each of said colors indicates a medical analysis or test to be performed on the synovial fluid in said collection tubes corresponding to said cap, said first collection tube including a chelating agent for testing for microscopy, mucin clot analysis and cell count, said second tube including Lithium heparin for testing for glucose, total protein, Lactate Dehydrogenase, uric acid, rheumatoid factor and complacent C3 and C4;
    at least one needle having a predetermined length adapted for aspirating the synovial fluid from the person's joint;
    at least one syringe adapted for connecting to said needle for aspirating the synovial fluid from the person's joint and placing in one of said collection tubes;
    said tray receptacles including at least one contoured collection tube tray receptacle for each of said collection tubes for isolating said collection tubes; each said collection tube tray receptacles including indentations for facilitating unobstructed grasping of said collection tubes;
    at least one iodine swabstick including iodine;
    at least one alcohol pad including alcohol;
    at least one absorption sponge, adapted for placement in said excess fluid tray receptacle, for absorbing and holding excess synovial fluid that remains in said syringe after the synovial fluid is placed in said collections tubes and to be discarded so as to prevent spillage, said sponge being expandable when absorbing the excess synovial fluid so as to at least partially fill said excess fluid tray receptacle, said sponge becoming a semi-solid gel when absorbing the excess synovial fluid;
    at least one mailing canister for transporting said collection tubes to the laboratory, said canister being devoid of an anticoagulant;
    said tray receptacles comprising at least one receptacle for holding said syringe, said receptacle for said syringe having a shape similar to said syringe, and a synovial fluid reservoir for holding said absorption sponge;
    a biohazard specimen bag for holding and transporting said canister, said biohazard specimen bag being devoid of an anticoagulant, said synovial fluid in said collection tubes not being temperature sensitive or pressure sensitive; and
    a fluid requisition form comprising colors corresponding to said first color, said second color and said third color of said collection tube caps; indicia on said form corresponding to each of said colors that identify the tests that need to be performed on the aspirated synovial fluid in each of said collection tubes having said cap color corresponding to one of said fluid requisition form colors for facilitating a prevention of a mistake.

2. A kit as recited in claim 1, further comprising:
sodium heparin in one of said collection tubes.

3. A kit as recited in claim 1, further comprising:
a second needle having a length adapted for administering an anesthetic.

4. A kit as recited in claim 1, further comprising:
an agent in at least one of said collection tubes that prevents clotting.

5. A kit as recited in claim 1, wherein said needle comprises:
an eighteen (18) gauge needle adapted for connecting to said syringe; said needle adapted for aspirating the synovial fluid from the person's joint, said syringe being approximately 50 cc.

6. A kit as recited in claim 1, further comprising:
an express mailing bag for mailing said collection tubes to the laboratory.

7. A kit as recited in claim 1, further comprising:
a liquid absorption pouch, storable in said mailing canister, for absorbing liquid that may spill: from any of said collection tubes.

8. A kit as recited in claim 1, further comprising:
at least one alcohol pad for cleaning an area on the patient to be pierced by said needle; and
a gram stain culture with sensitivity and Lyme disease titers.

9. A kit as recited in claim 1, wherein said receptacles comprise: a second syringe contoured receptacle shaped like a syringe so as to secure a second.

10. A kit as recited in claim 1, wherein said tray comprises:
a second collection tube contoured receptacle shaped like said second collection tube so as to individually secure said second collection tube.

11. A kit as recited in claim 1, wherein said tray comprises:
a third collection tube contoured receptacle shaped like said third collection tube so as to individually secure said third collection tube.

12. A kit as recited in claim 1, wherein said receptacles comprise:
  an absorption sponge contoured receptacle shaped like the absorption sponge, said absorption sponge contoured receptacle adapted to secure said absorption sponge after it expands.

13. A kit as recited in claim 12, wherein said absorption sponge contoured receptacle further comprises:
  the synovial fluid reservoir.

14. A method for performing an arthrocentesis procedure that aspirates synovial fluid from a person's joint, delivering collected synovial fluid to a laboratory for analysis and receiving laboratory tests results, said method comprising the steps of:
  providing a kit having:
  a tray, said tray having a plurality of tray receptacles;
  said tray receptacles including an excess fluid tray receptacle for placing excess synovial fluid aspirated from a person;
  a gauze pad, storable in said tray;
  a plurality of collection tubes for holding the synovial fluid aspirated from the person's joint, said tubes including a first collection tube having a first removable cap having a first color, a second collection tube having a second removable cap having a second color and a third collection tube having a third removable cap having a third color; said first color, said second color and said third color comprising different colors wherein each of said colors indicates a medical analysis or test to be performed on the synovial fluid in said collection tubes corresponding to said cap; said first collection tube including a chelating agent for testing for microscopy, mucin clot analysis and cell count, said second tube including lithium heparin for testing for glucose, total protein, Lactate Dehydrogenase, uric acid, rheumatoid factor and complacent C3 and C4;
  an agent in at least one of said collection tubes that prevents clotting;
  at least one needle having a predetermined length adapted for withdrawing the synovial fluid from the person's joint;
  at least one syringe adapted for connecting to said needle for aspirating the synovial fluid from the person's joint and placing in one of said collection tubes;
  said tray receptacles including at least one contoured tray receptacle for each of said collection tubes for isolating said collection tubes, each said collection tube tray receptacles including indentations for facilitating unobstructed grasping of said collection tubes;
  at least one iodine based swabstick;
  at least one absorption sponge adapted for placement in said excess fluid tray receptacle, for absorbing and holding mid excess synovial fluid that remains in said syringe after the synovial fluid is placed in said collections tubes and to be discarded so as to prevent spillage, said sponge being expandable when absorbing said excess synovial fluid so as to at least partially fill said excess fluid tray receptacle, said sponge becoming a semi-solid gel when absorbing said excess synovial fluid;
  at least one mailing canister for transporting said tubes to the laboratory; said canister being devoid of an anticoagulant;
  an express mailing bag for mailing said tubes to a laboratory; and
  a fluid requisition form identifying the tests that need to be done on the aspirated synovial fluids;
  drawing the synovial fluid from the person using said needle and placing a sample in at least one tube;
  placing said synovial fluid in at least one of said collection tubes;
  entering information regarding test required on said synovial fluid on said fluid requisition form;
  placing said at least one collection tube with said synovial fluid and said at least one absorption sponge in said mailing canister; and
  placing said at least one collection tube and said fluid requisition form in said express mailing bag.

15. A method as recited in claim 14, further comprising the step of:
  providing a biohazard specimen bag for holding and transporting said mailing canister, said mailing canister being devoid of an anticoagulant, said synovial fluid in said collection tubes not being temperature or pressure sensitive.

16. A method as recited in claim 14, further comprising:
  a liquid absorption pouch, storable in said mailing canister for absorbing liquid that may spill from any of said collection tubes.

17. A method as recited in claim 14, wherein said agent in said at least one collection tube comprises sodium heparin.

18. A method as recited in claim 14, wherein said fluid requisition form comprises:
  color codes corresponding to said first color, said second color and said third color of said removable caps for identifying tests that need to be performed on the aspirated fluid in each of said collection tubes having said cap color corresponding to one of said fluid requisition form color codes and for facilitating prevention of a mistake in filling out said form and performing tests on the synovial fluid.

\* \* \* \* \*